United States Patent [19]

Roizman et al.

[11] Patent Number: 5,834,216
[45] Date of Patent: Nov. 10, 1998

[54] SCREENING METHODS FOR THE IDENTIFICATION OF INDUCERS AND INHIBITORS OF PROGRAMMED CELL DEATH (APOPTOSIS)

[75] Inventors: Bernard Roizman; Joany Chou, both of Chicago, Ill.

[73] Assignee: Arch Development Corporation, Chicago, Ill.

[21] Appl. No.: 524,344

[22] Filed: Sep. 6, 1995

[51] Int. Cl.$^6$ .......................... G01N 33/53; G01N 3/561; C12Q 1/12
[52] U.S. Cl. ........................ 435/7.21; 435/15; 436/516
[58] Field of Search .................................. 435/4, 7.1, 15, 435/7.21; 436/516

[56] References Cited

U.S. PATENT DOCUMENTS 4,769,331  9/1988  Roizman et al. ..................... 435/172.3

FOREIGN PATENT DOCUMENTS

| 243155 | 10/1987 | European Pat. Off. |
| 453242 | 10/1991 | European Pat. Off. |
| WO 92/04050 | 3/1992 | WIPO |
| WO 93/19591 | 10/1993 | WIPO |

OTHER PUBLICATIONS

V.A. Polunovsky et al., "Oncogenic upregulation of translation initiation factor eIF–4E activates Bc1–2 and prevents growth factor dependent apotosis in normal and Myc–deregulated fibroglast," Molecular Biology of the Cell, p. 252a (Dec. 10–14, 1994).
Kochi et al. (1993) Exp. Cell Res. vol. 208C1) 296–302.
Ackermann et al., Characterization of Herpes Simplex Virus 1 α Proteins 0, 4, and 27 with Monoclonal Antibodies, *J. Virol.*, 52(1):108–118 (1984).
Ackermann et al., Identification by Antibody to a Synthetic Peptide of a Protein Specified by a Diploid Gene Located in the Terminal Repeats of the L Component of Herpes Simplex Virus Genome, *J. Virol.*, 58(3):843–850 (1986).
Barinaga, M., Cell Suicide: By ICE, Not Fire, *Science*, 263:754–756 (1994).
Centifano–Fitzgerald et al., Ocular Disease Pattern Induced by Herpes Simplex Virus is Genetically Determined by a Specific Region of Viral DNA*, *J. Exp. Med.*, 155:475–489 (1983).
Chou and Roizman, Isomerization of Herpes Simplex Virus 1 Genome: Identification of the cis–Acting and Recombination Sites within the Domain of the α Sequence, *Cell*, 41:803–811 (1985).
Chou and Roizman, The Terminal α Sequence of the Herpes Simplex Virus Genome Contains the Promoter of a Gene Located in the Repeat Sequences of the L Component, *J. Virol.*, 57(2):629–637 (1986).
Chou and Roizman, The Herpes Simplex Virus 1 Gene for ICP34.5, Which Maps in Inverted Repeated, Is Conserved in Several Limited–Passage Isolates but Not in Strain 17syn+, *J. Virol.*, 64(3):1014–1020 (1990).

Chou and Roizman, *J. Cell Biochem.*, Keystone Symposia, Supplement 10C, Feb. 21–Mar. 2, 1992, Abstract N303, p. 136.
Chou and Roizman, The γ134.5 gene of herpes simplex virus 1 precludes neuroblastoma cells from triggering total shutoff of protein synthesis characteristic of programmed cell death in neuronal cells, *PNAS USA*, 89:3266–3270, Apr. 1992.
Chou et al., Mapping of Herpes Simplex Virus–1 Neurovirulence to γ134.5, a Gene Nonessential for Growth in Culture, *Science*, 250:1262–1266 (1990.
Clem et al., Prevention of Apoptosis by a Baculovirus Gene During Infection of Insect Cells, *Science*, 254:1388–1389, Nov. 29, 1991.
Corey and Spear, Infections With Herpes Simplex Viruses (First of Two Parts), *N. Eng. J. Med.*, 314:686–691 (1986).
DeLuca et al., Isolation and Characterization of Deletion Mutants of Herpes Simplex Virus Type 1 in the Gene Encoding Immediate–Early Regulatory Protein ICP4, *J. Virol.*, 56(2):558–570 (1985).
Ejercito et al., Characterization of Herpes Simplex Virus Strains Differing in their Effects on Social Behaviour of Infected Cells, *J. Gen. Virol.*, 2:357–364 (1986).
Gagliardini et al., Prevention of Vertebrate Neuronal Death by the crmA Gene, *Science*, 263:826–828 (1994).
Gregory et al., Activation of Epstein–Barr virus latent genes protects human B cells from death by apoptosis, *Nature*, 349:612–614 (1991).
Hayward et al., Anatomy of herpes simplex virus DNA: Evidence for four populations of molecules that differ in the relative orientations of their long and short components, *Proc. Natl. Acad. Sci. USA*, 72(11):4243–4247 (1975).
Henderson et al., Induction of bcl–2 Expression by Epstein–Barr Virus Latent Membrane Protein 1 Protects Infected B Cells From Programmed Cell Death, *Cell*, 65:1107–1115 (1991).
Honess and Roizman, Proteins Specified by Herpes Simplex Virus, *J. Virol.*, 12(6):1347–1365 (1973).
Hubenthal–Voss et al., Mapping of Functional and Antigenic Domains of the α4 Protein of Herpes Simplex Virus 1, *J. Virol.*, 62(2):454–462 (1988).
Itoh et al., The Polypeptide Encoded by the cDNA for Human Cell Surface Antigen Fas Can Mediate Apoptosis, *Cell*, 66:233–243 (1991).
Javier et al., Genetic and Biological Analyses of a Herpes Simplex Virus Intertypic Recombinant Reduced Specifically for Neurovirulence, *J. Virol.*, 65:1978–1984, (1987).
Johnson et al., Why do Neurons Die When Deprived of Trophic Factor?, *Neurobiol. of Aging*, 10:549–552 (1989).

(List continued on next page.)

Primary Examiner—Christina Y. Chan
Assistant Examiner—Emma Cech
Attorney, Agent, or Firm—Marshall, O'Toole, Gerstein, Murray & Borun

[57] ABSTRACT

Methods for the identification of inducers and inhibitors of apoptosis are described. The method exploits the finding that the exposure of cells to apoptotic stress and its concurrent shutdown of cellular protein synthesis is accompanied by phosphorylation of IF-2α and a novel protein termed p90.

17 Claims, 4 Drawing Sheets

OTHER PUBLICATIONS

Katz et al., Quantitative Polymerase Chain Reaction Analysis of Herpes Simplex Virus DNA in Ganglia of Mice with Replication–Incompetent Mutants, *J. Virol.*, 64(9):4288–4295.

Kyte et al., A Simple Method for Displaying the Hydropathic Character of a Protein, *J. Mol. Biol.*, 157:105–132 (1982).

Loo et al., Serial Passage of Embryonic Human Astrocytes in Serum–Free, Hormone–Supplemented Medium, *J. Neuroscience Research*, 28:101–109 (1991).

Lord et al., Sequence of MyD116 cDNA: a novel myeloid differentiation primary response gene induced by IL6, *Nucleic Acid Res.* 18(9):2823 (1990).

Mackem and Roizman, Structural Features of the Herpes Simplex Virus α Gene 4, 0, and 27 Promoter–Regulatory Sequences Which Confer α Regulation on Chimeric Thymidine Kinase Genes, *J. Virol.*, 44(3):934–947 (1982).

Markert et al., Expanded spectrum of viral therapy in the treatment of nervous system tumors, *J. Neurosurg.*, 77:590–594 (1992).

Markert et al., Experimental Glioma Therapy with Attenuated Thymidine–Kinase Proficient Herpes Simplex Mutants, Dept. of Neuro., Harvard Med. School, Research Manuscript, 18 pgs. (1992).

Markert et al., Reduction and Elimination of Encephalitis in an Experimental Glioma Therapy Model with Attenuated Herpes Simplex Mutants that Retain Susceptibility to Acyclovir, *Neurosurgery*, 32(4):597–603 (1993).

Martuza et al., Experimental Therapy of Human Glioma by Means of a Genetically Engineered Virus Mutant, *Science*, 252:854–856 (1991).

McGeoch et al., The Complete DNA Sequence of the Long Unique Region in the Genome of Herpes Simplex Virus Type 1, *J. Gen. Virol.*, 69:1531–1574 (1988).

Meignier et al., In Vivo Behavior of Genetically Engineered Herpes Simplex Viruses R7017 and R7020: Construction and Evaluation in Rodents, *J. Infect. Dis.*, 158(3):602–614 (1988).

Peppel and Baglioni, A Simple and Fast Method to Extract RNA from Tissue Culture Cells, *BioTechniques*, 9(6):711–712 (1990).

Post and Roizman, A Generalized Technique for Deletion of Specific Genes in Large Genomes: α Gene 22 of Herpes simplex Virus 1 Is Not Essential for Growth, *Cell*, 25:227–232 (1981).

Rawson et al., Death of Serum–free Mouse Embryo Cells Caused by Epidermal Growth Factor Deprivation, *J. Cell. Biol.*, 113(3):671–679 (1991).

Renfranz et al., Region–Specifc Differentiation of the Hippocampal Stem Cell Line HiB5 upon Implantation into the Developing Mammalian Brain, *Cell*, 66:713–729 (1991).

Roizman, Herpesviridae: A Brief Introduction, *Field's Virology*, Second Edition, 64: 1787–1793 (1990).

Roizman, Multiplication of Viruses, *Field's Virology*, Second Edition, 5:87–94 (1991).

Roller and Roizman, Herpes Simplex Virus 1 RNA–Binding Protein $U_s11$ Negatively Regulates the Accumulation of a Truncated Viral mRNA, *J. Virol.*, 65(11):5873–5879 (1991).

Ryder et al., Establishment and Characterization of Multipotent Neural Cell Lines Using Retrovirus Vector–Mediated Oncogene Transfer, *J. Neurobiol.*, 21(2):356–375 (1990).

Sentman et al., bcl–2 Inhibits Multiple Forms of Apoptosis but Not Negative Selection in Thymocytes, *Cell*, 67:879–888, Nov. 29, 1991.

Snyder et al., Multipotent Neural Cell Lines Can Engraft and Participate in Development of Mouse Cerebellum, *Cell*, 68:33–51 (1992).

Strasser et al., Bcl–2 Transgene Inhibits T Cell Death and Perturbs Thymic Self–Censorship, *Cell*, 67:889–899, Nov. 29, 1991.

Taha et al., A Variant of Herpes Simplex Virus Type 2 Strain HG52 with a 1.5 kb Deletion in $R_L$ between 0 to 0.02 and 0.81 to 0.83 Map Units Is Non–neurovirulent for Mice, *J. Gen. Virol.*, 70:705–716 (1989).

Wadsworth et al., Anatomy of Herpes Simplex Virus DNA II. Size, Composition, and Arrangement of Inverted Terminal Repetitions, *J. Virol.*, 15(6):1487–1497 (1975).

Whitlay et al., Replication, Establishment of Latency, and Induced Reactivation of Herpes Simplex Virus $\gamma_1$ 34.5 Deletion Mutants in Rodent Models, *J. Clin. Invest.*, 91:2387–2843, (1993).

Williams, Programmed Cell Death: Apoptosis and Oncogenesis, *Cell*, 65:1097–1098 (1991).

Alexianu et al., "Apoptotic Cell Death of a Hybrid Motoneuron Cell Line Induced by Immunoglobulins from Patients with Amyotrophic Lateral Sclerosis," *J. Neurochem.*, 63:2365–2368 (1994).

Chou et al., "Herpes Simplex Virus 1 $Gamma_1 34.5$ Gene Function, Which Blocks the Host Response to Infection, Maps in the Homologous Domain of the Genes Expressed During Growth Arrest and DNA Damage," *Proc. Nat'l Acad. Sci., USA*, 91:5247–5251 (Jun., 1994).

Fornance et al., "Genotoxic–Stress–Response Genes and Growth–Arrest Genes," *Ann. N.Y. Acad. Sci.*, 663:139–153 (1992).

Fornance et al., "Mammalian Genes Coordinately Regulated by Growth Arrest Signals and DNA–Damaging Agents," *Mol. Cell. Biol.*, 9(10):4196–4203 (Oct., 1989).

Gross et al., "Identification of a $M_r = 39,000$ Phosphoprotein in Highly Purified Preparations of Rabbit Reticulocyte eIF–2 That is Distinct from the $M_r = 35,000$ Subunit Phosphorylated by the Hemin–Controlled Translational Repressor," *J. Biol. Chem.*, 255(13):6270–6275 (Jul. 10, 1980).

Gschwind et al., "Apoptotic Cell Death Induced by β–Amyloid$_{1-42}$ Peptide Is Cell Type Dependent," *J. Neurochem.*, 65:292–300 (1995).

Hershey, J.W.B., "Translational Control in Mammalian Cells," *Annu. Rev. Biochem.*, 60:717–755 (1991).

LaFerla et al., "The Alzheimer's Aβ Peptide Induces Neurodegeneration and Apoptotic Cell Death in Transgenic Mice," *Nat. Genet.*, 9(1):21–30 (Jan., 1995).

Maurides et al., "Evaluation of Protein Phosphorylation State by a Combination of Vertical Slab Gel Isoelectric Focusing Immunoblotting," *Anal. Biochem.*, 183:144–151 (1989).

McGeoch et al., "Neurovirulence Factor," *Nature(London)*, 353:609 (Oct. 17, 1991).

McKie et al., "Characterization of the Herpes Simplex Virus Type 1 Strain 17[+] Neurovirulence Gene RL1 and Its Expression in a Bacterial System," *J. Gen. Virol.*, 75:733–741 (1994).

Merrick, W.C., "Mechanism and Regulation of Eukaryotic Protein Synthesis," *Microb. Rev.*, 56(2):291–315 (Jun., 1992).

Pathak et al., "Generation of a Mutant Form of Protein Synthesis Initiation Factor eIF–2 Lacking the Site of Phosphorylation by eIF–2 Kinases," *Mol. Cell Biol.,* 8(2):993–995 (Feb., 1988).

Portera–Cailliau et al., "Evidence for Apoptotic Cell Death in Huntington Disease and Excitotoxic Animal Models," *J. Neurosci.,* 15(5):3775–2787 (May, 1995).

Roy et al., "The Gene for Neuronal Apoptosis Inhibitory Protein Is Partially Deleted in Individuals with Spinal Muscular Atrophy," *Cell,* 80:165–178 (Jan. 13, 1995).

Sarre, T.F., "The Phosphorylation of Eukaryotic Initiation Factor 2: A Principle of Translational Control in Mammalian Cells," *BioSystems,* 22:311–325 (1989).

Scorsone et al., "Phosphorylation fo Eukaryotic Initiation Factor 2 During Physiological Stresses Which Affect Protein Synthesis," *J. Biol. Chem.,* 262(30):14538–14543 (Oct. 25, 1987).

Zhan et al., "The gadd and MyD Genes Define a Novel Set of Mammalian Genes Encoding Acidic Proteins That Synergistically Suppress Cell Growth," *Mol. Cell. Biol.,* 14(4):2361–2371 (Apr., 1994).

SCREENING METHODS FOR THE IDENTIFICATION OF INDUCERS AND INHIBITORS OF PROGRAMMED CELL DEATH (APOPTOSIS)

The government may own certain rights in the present invention pursuant to grants from the National Cancer Institute (CA47451), from the National Institute for Allergy and Infectious Diseases (AI24009), and the United States Public Health Service.

BACKGROUND OF THE INVENTION

The idea that cells are internally programmed to die at a certain point in their life cycle has generated considerable interest in the scientific community. Programmed cell death, or apoptosis is an active cellular mechanism and has several important implications. First, it is clear that such an active process can provide additional means for regulating cell numbers as well as the biological activities of cells. Secondly, mutations or cellular events which potentiate apoptosis may result in premature cell death. Third, a form of cell death which is dependent on a specific active cellular mechanism can at least potentially be suppressed. Finally, inhibition of programmed cell death may be expected to lead to aberrant cell survival and could be expected to contribute to oncogenesis, while conversely it is thought that tumor cell suicide may be induced through apoptosis.

In general, apoptosis involves distinctive morphological changes including nuclear condensation and degradation of DNA to oligonucleosomal fragments. In certain circumstances it is evident that apoptosis is triggered by or is preceded by changes in protein synthesis. For example, cellular protein synthesis may be significantly down-regulated. The DNA degradation described above may be a slow process, occurring days after the cessation of the cell's biosynthetic activities. Apoptosis appears to provide a very clean process for cellular destruction, in that the cells are disposed of by specific recognition and phagocytosis prior to bursting. In this manner cells can be removed from a tissue without causing damage to the surrounding cells. Thus, it can be seen that programmed cell death is important to a number of physiological processes, including morphological development, clonal selection in the immune system, and normal cell maturation and death in other tissue and organ systems.

It has also been demonstrated that cells can undergo apoptosis in response to environmental information. Examples include the appearance of a stimulus, such as glucocorticoid hormones for immature thymocytes, or the disappearance of a stimulus, such as interleukin-2 withdrawal from mature lymphocytes, or the removal of colony stimulating factors from hemopoietic precursors (for a review of literature see Williams, Cell, 65:1097–1098 [1991]). Furthermore, it has recently been demonstrated that the response to removal of nerve growth factor from established neuronal cell cultures that mimics target removal, or axiotomy, or other methods of trophic factor removal, is a triggering of a suicide program or programmed cell death. [See Johnson et al., Neurobiol. of Aging, 10:549–552 (1989) ]. The authors propose a "death cascade" or "death program," which envisions that trophic factor deprivation initiates the transcription of new mRNA and the subsequent translation of that mRNA into death associated proteins which act in sequence to ultimately produce "killer proteins." Such an intracellular mechanism seems to fit well with the characteristics of apoptosis discussed above, e.g., death of specific cells without the release of harmful materials and without the disruption of tissue integrity. Furthermore, the authors indicate that inhibitors of macromolecular synthesis prevented the death of neurons in the absence of nerve growth factor.

Studies have been conducted to explore the possibility that tumor cells could be eliminated by artificially triggering apoptosis. The anti-APO-1 monoclonal antibody induces apoptosis in several transformed human B and T cell lines. The antibody binds to a 52 kd surface protein and could act either by mimicking a positive death-inducing signal or by blocking the activity of a factor required for survival. Anti-FAS antibodies have similar effects. The recent cloning and sequencing of the gene for the FAS antigen has shown that it is a 63 kilodalton transmembrane receptor. Itoh et al., Cell, 66:233–243 (1991).

However, it is important to note that neither APO-1 nor FAS are likely to function exclusively as triggers for cell death. Both are cell surface receptors that may activate quite different cellular responses under other circumstances. Moreover, these antigens are not confined to tumor cells and their effect on normal cells is certainly an important consideration, as is the possible appearance of variants that no longer display the antigens.

It has also been demonstrated that the cell death induced by a range of cytotoxic drugs, including several used in cancer therapy, has also been found to be a form of apoptosis [Barry et al, Biochem. Biopharmacol., 40:2353–2362 (1990) ]. This is also true, in many cases, for cell death after gamma- or x-irradiation [Williams, Cell, 65:1097–1098 (1991)]. In fact, the failure of apoptosis in tumor cells could be of fundamental importance in contributing not only to the evasion of physiological controls on cell numbers, but also to resistance both to natural defenses and to clinical therapy.

It has also been demonstrated that expression of the bcl-2 gene can inhibit death by apoptosis. The bcl-2 gene was isolated from the breakpoint of the translocation between chromosomes 14 and 18 found in a high proportion of the most common human lymphomas, that being follicular B cell lymphomas. The translocation brings together the bcl-2 gene and immunoglobulin heavy chain locus, resulting in an aberrantly increased bcl-2 expression in B cells. Subsequently, Henderson et al., [Cell, 65:1107–1115 (1991)] demonstrated that expression of latent membrane protein 1 in cells infected by Epstein-Barr virus protected the infected B cells from programmed cell death by inducing expression of the bcl-2 gene. Sentman et al. [Cell, 67: 879–888 (1991)] demonstrated that expression of the bcl-2 gene can inhibit multiple forms of apoptosis but not negative selection in thymocytes. Strasser et al. [Cell, 67:889–899 (1991)] demonstrated that expression of a bcl-2 transgene inhibits T cell death and can perturb thymic self-censorship. Clem et al. [Science, 245:1388–1390 (1991)] identified a specific baculovirus gene product as being responsible for blocking apoptosis in insect cells. Gagliardini et al [Science, 263:826–828 (1994)] demonstrated the ability of the crmA gene product to prevent apoptosis in the dorsal root ganglion cells of chicken which had been deprived of nerve growth factor. More generally, Barinaga, [Science, 263:754–756 (1994)] also discusses the role of bcl-2, Bax(long), bclX (short) and ICE in apoptosis.

A number of diseases have been associated with apoptosis of neuronal cells. For example, amyotrophic lateral sclerosis (Lou Gehrig's disease) has been associated with apoptotic cell death. Alexianu et al., J. Neurochem. 63:2365–2368 (1994). Spinal muscular atrophy is associated with the partial deletion of an apoptosis inhibitory protein which results in apoptotic cell death. Roy et al., *Cell* 80:167–178 (1995). Huntington's disease has also been associated with apoptotic cell death. Portera-Cailliau et al., *J. Neurosci* 15:3775–3787 (1995). Apoptotic cell death has also been strongly implicated in Alzheimer's disease, Gschwind et al., *J. Neurochem* 65:292–300 (1995); and LaFerla et al., *Nat. Genet.* 9:21–30 (1995).

Thus it is clear that the ability to control apoptosis either by inducing it to occur in cells (e.g. in tumor cells) or to prevent apoptosis, (e.g. in neurodegenerative conditions since as Alzheimer's disease, amyotrophic lateral sclerosis, Huntington's disease, spinal muscle atrophy, and other neurodegenerative disorders) will allow therapeutic intervention in diseases for which there are currently few if any therapeutic modalities. In order to achieve such therapeutic control, screening methods must be made available for the screening of candidate substances which may either induce or inhibit apoptosis.

Herpes simplex viruses have particular characteristics that make them useful for the study of apoptosis (see, WO 93/19591 published 14 Oct., 1993 and references cited below, all of which are incorporated herein by reference). Herpes simplex virus 1 (HSV-1) encodes a gene, $\gamma_1 34.5$, whose function is to preclude a host response which terminates all protein synthesis subsequent to the onset of viral DNA synthesis [Chou et al., *Proc. Natl. Acad. Sci. USA* 89:3266–3270 (1992)]. The $\gamma_1 34.5$ gene maps in the sequences flanking the long unique sequence of HSV-1 DNA and therefore is present in two copies per genome [Chou et al., *J. Virol.* 57:629–637 (1986)]. The 263 amino acid protein encoded by the HSV-1(F) $\gamma_1 34.5$ consists of 3 domains, an amino terminal domain of 160 amino acid-domain, 10 repeats of three amino acids (AlaThePro), and a 73 amino acid-carboxyl terminal domain [Chou et al., *J. Virol.* 64:1014–1020 (1990)]. A stretch of 64 amino acids at the carboxyl terminus of the $\gamma_1 34.5$ is homologous to a corresponding stretch of amino acids of the carboxyl terminus of a murine protein known as MyD116 and a Chinese hamster protein known as GADD34 [Chou et al., *Proc. Natl. Acad. Sci. USA* 89:3266–3270 (1992); McGeoch et al., *Nature (London)* 353:609 (1991)]. MyD116 is a member of a set of proteins induced in myelogenous leukemia cells induced for terminal differentiation by interleukin 6 [Lord et al., *Nucleic Acids Res.* 18:2823 (1990)]. GADD34, structurally closely related to MyD116, is also one of a subset of proteins induced following DNA damage or cell growth arrest [Fornace et al., *Mol. Cell. Biol.* 9:4196–4203 (1989); Fornace et al., *Ann. N.Y. Acad. Sci.* 663:139–153 (1992); Zhan et al., *Mol. Cell. Biol.* 14:2361–2371 (1994)].

Infection of a human cells with Herpes simplex virus in which both copies of $\gamma_1 34.5$ are inactivated or deleted, but particularly of human neuroblastoma cell line SK-N-SH or primary human foreskin fibroblasts results in nearly complete cessation of host cell protein synthesis replicative cycle [Chou et al., *J. Virol.* 66:8304–8311 (1994)]. This total premature shutoff of protein synthesis is not seen in these cells when they are treated with inhibitors of viral DNA synthesis or in Vero cells [Chou et al., *Proc. Natl. Acad. Sci. USA* 89:3266–3270 (1992)].

The capacity to preclude total premature shutoff of protein synthesis maps in the carboxyl terminus domain of $\gamma_1 34.5$ protein that is homologous to the MyD116 protein [Chou et al., *Proc. Natl. Acad. Sci. USA* 91:5247–5251 (1994)]. Indeed, the carboxyl terminus of MyD116 successfully substitutes for the corresponding domain of $\gamma_1 34.5$. The viruses lacking the $\gamma_1 34.5$ or unable to express the carboxyl terminus of protein are totally avirulent in a murine encephalitis model of HSV-1 infections [Chou et al., *Science* 250:1262–1266 (1990); Whitley et al., *J. Clin. Invest.* 91:2837–2843 (1993); McKie et al., *J. Gen. Virol.* 75:733–741 (1994)].

The premature shut off of protein synthesis raises several interesting questions, i.e. what triggers the host response, what is the mechanism by which protein synthesis is turned off, the mechanism by which $\gamma_1 34.5$ precludes the host response. The Examples set out below show the first demonstration that the activity of a protein kinase responsible for the phosphorylation of the $\alpha$ subunit of the translation initiation factor eIF-2 and the phosphorylation of a $M_r$ 90,000 protein which has been designated as p90 co-precipitated with anti-PKR antibody are selectively increased in cells infected with mutants lacking the $\gamma_1 34.5$ gene. The present invention exploits these observations by providing methods for screening candidate substances for their ability to induce apoptosis or to inhibit apoptosis as illustrated by their ability to induce phosphorylation of eIF-2$\alpha$ and/or p90 or by their ability to prevent apoptosis induced phosphorylation of eIF-2$\alpha$ and/or p90.

SUMMARY OF THE INVENTION

The present invention is directed to methods for screening candidate inducers or inhibitors of apoptosis. The methods of the invention exploit the observed phenomenon that cells whose protein synthesis is shut down as the result of stress including apoptotic stress exhibit increased ability to phosphorylate eIF-2$\alpha$ and/or a novel protein referred to herein as p90.

More particularly, the present invention is directed to a method for screening candidate inhibitors of apoptosis comprising preparing duplicate cell cultures, exposing one of the duplicate cultures to the candidate inhibitor; exposing both of the duplicate cultures to apoptotic stress; preparing respective cell lysates from the duplicate cultures; contacting the cell lysates ATP wherein the ATP has a $\gamma$-phosphate having a detectable label, or an analog of a $\gamma$ phosphate (i.e., having a label are capable of being transferred to a phosphorylation site such as $\gamma S^{35}$); measuring the levels of phosphorylated (labeled) eIF-2$\alpha$ and/or p90; and wherein an inhibitor of apoptosis is identified by its ability to prevent or decrease phosphorylation (labeling) of eIF-2$\alpha$ and/or p90.) Examples of apoptotic stress include but are not limited to infection with herpesviruses lacking expressible $\gamma_1 34.5$ genes, deprivation of growth factors from the medium, treatment with cytotoxic drugs.

Cells most useful in the practice of the foregoing method include human cells. More particularly cells useful in the method are human foreskin fibroblasts, HeLa cells, SK-N-H neuroblastoma cells and other human cell lines.

Inducers capable of inducing apoptosis include but are not limited to $\gamma_1 34.5$-deficient mutants of herpes viruses and environmental stresses such as deprivation of growth factors, ultraviolet- or x-irradiation, and others.

Phosphorylation or (labeling) of eIF-2$\alpha$ and p90 may be measured by precipitating the cell lysates with an antibody specific for PKR or antibodies specific for eIF-2$\alpha$ or p90. The antibodies may be monoclonal antibodies or polyclonal antibodies.

After precipitation, phosphorylated (labeled) eIF-2$\alpha$ and/or phosphorylated p90 may be separated from other cellular proteins by electrophoresis or by chromatographic methods. By way of example, labeled eIF-2$\alpha$ and p90 may be separated on denaturing polyacrylamide gels after which the separated proteins may be transferred to, for example, a nylon or nitrocellulose membrane followed by exposure to X-ray film. Relative levels of phosphorylation are then determined after developing the exposed X-ray film and quantifying the density of bands corresponding to eIF-2α and/or p90 by, for example, densitometry. The autoradiograph may also be used to localize the bands on the membrane corresponding to labelled eIF-2α and p90 after which they may be excised from the membrane and counted by liquid scintillation or other counting methods. Using the method described above, an inhibitor of apoptosis is identified by its ability to prevent or to decrease phosphorylation of eIF-2α and/or p90 after apoptotic stress when compared to control cells not exposed to the inhibitor.

The invention is also directed to methods for screening candidate inducers of apoptosis which are useful, for example, in the treatment of tumorigenic disease. The methods are similar to those described above. More specifically, duplicate cell cultures are prepared as described above. One of the duplicate cultures is then exposed to the candidate inducer. Cells are then analyzed for the phosphorylation labeling of eIF-2α and p90 as described above. An apoptosis inducer is identified by its ability to increase a cell's capability to phosphorylate (label) eIF-2α and/or p90.

The invention is also directed to DNA encoding p90, and vectors comprising DNA encoding p90 including expression vectors capable of expressing the p90 protein, and the therapy vectors useful for the introduction of DNA encoding p90 into the genome of a cell either by random recombination or by homologous recombination. Also contemplated by the present invention are cells transfected with the vectors of the present invention. Such cells are useful in producing increased quantities of p90 then would be otherwise available form cells expressing endogenous p90 genes.

Vectors comprising p90 may also be used therapeutically. For example certain tumors may result form the inability of tumor cells to appropriately regulate cell growth as the result of a mutation in a p90 gene. In such a case, vectors of the present invention may be introduced into the tumor cells thereby providing the tumor cells with sufficient p90 to undergo apoptosis.

DETAILED DESCRIPTION

Figure 1A:
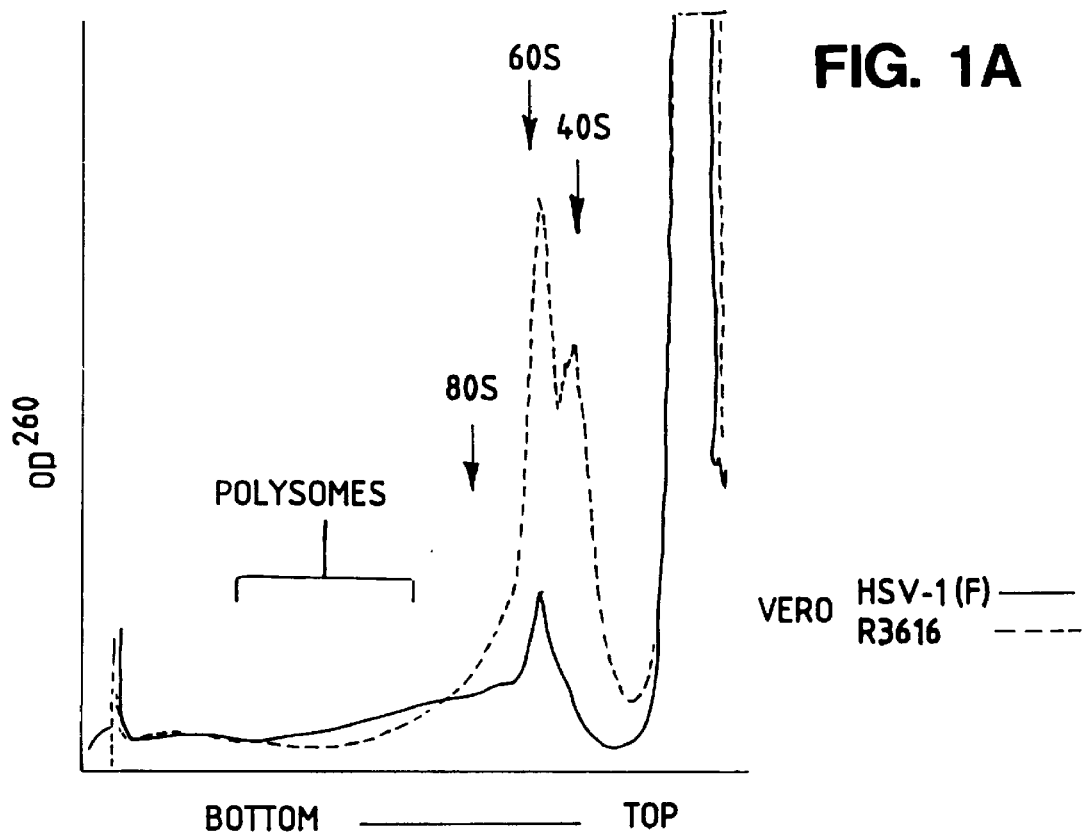
FIGS. 1A–1B illustrate the UV optical density profiles of cytoplasmic fraction from Vero or human SK-N-SH neuroblastoma cells infected with wild type or mutant viruses.

Infection of SK-N-SH and other cells with herpes simplex viruses lacking $\gamma_1 34.5$ genes capable of expressing an active gene product results in the premature shut off of cellular protein synthesis. The Examples set out below discuss the mechanisms by which this shut down occurs and how these mechanisms have been exploited in developing methods for screening candidate inhibitors and inducers of apoptosis.

The following Examples are presented by way of illustration and are not intended to limit the scope of the invention as set out in the appended claims.

Example 1 describes the cells and viruses used in the studies.

Example 2 illustrates the sedimentation profile of polyribosomes of cells infected with wild type or $\gamma_1 34.5^-$ viruses.

Example 3 demonstrates that viral mRNA is not degraded in $\gamma_1 34.5^-$ virus infected cells.

Example 4 shows that lysates of HeLa cells infected with $\gamma_1 34.5^-$ virus contain a ribosome associated kinase which phosphorylated the eIF-2α of exogenously added eIF-2.

Example 5 demonstrates that the phosphorylation of eIF-2α is associated with a kinase present in a fraction enriched for ribosomes of cells infected with R3616 ($\gamma_1 34.5^-$ and in which protein synthesis was shut off, and shows that immunoprecipitation of PKR from the same fraction after reaction with [$\gamma^{32}$P]-ATP yielded several phosphorylated polypeptides.

Example 6 describes methods for screening candidate inhibitors and inducers of apoptosis.

Example 7 describes cloning DNA encoding p90.

EXAMPLE 1

CELLS AND VIRUSES

African Green Monkey kidney cells (Vero), HeLa cells, and the human neuroblastoma cells (SK-N-SH) from American Type Culture Collection were propagated in Dulbecco's modified Eagle's medium supplemented with 5% and 10% fetal bovine serum, respectively. HSV-1(F) is the prototype HSV-1 strain used in these studies (Ejercito et al., *J. Gen. Virol.* 2:357–364 (1968)). The HSV-1 recombinants R3616, R4002, and R3939 have been described [Chou et al., *Proc. Natl. Acad. Sci. USA* 89:3266–3270 (1992); Chou et al., *Proc. Natl. Acad. Sci. USA* 91:5247–5251 (1994)]. R3616 virus lacks 1 Kb from the coding domains of both copies of $\gamma_1 34.5$ genes. R4002 lacks 500 bp from the coding domain of thymidine kinase, ($U_L 23$) gene, and the first 28 codons from both copies of the $\gamma_1 34.5$ gene located at the 3' end of the α27-tk chimeric gene, is the promoter and first codon of the $U_L 22$ gene (encoding glycoprotein gH). In R4002, the α27-tk chimeric gene was inserted into both copies of the $\gamma_1 34.5$ gene such that the initiation codon of $U_L 22$ is in frame and adjacent to the 28th codon of the $\gamma_1 34.5$ gene. As a result, the $\gamma_1 34.5$ gene has a slightly stronger promoter and its protein has a truncated amino terminus. R3939 virus contains a six-way stop codon inserted in the DraIII site of the $\gamma_1 34.5$ gene and therefore its carboxyl terminal domain is not expressed. See also, WO 93/19591 published 14 Oct., 1993.

EXAMPLE 2

THE SEDIMENTATION PROFILES OF POLYRIBOSOMES EXTRACTED FROM THE CYTOPLASM OF VERO CELLS OR NEUROBLASTOMA CELLS INFECTED WITH HSV-1(F) (WILD TYPE) OR R3616 ($\gamma_1 34.5^-$) VIRUSES Investigation into the mechanism by which the apoptotic stress induced by infection with certain herpesviruses drastically inhibits cellular protein synthesis were undertaken.

One set of studies was conducted to evaluate that status of polyribosomes in Vero cells and in SK-N-SH neuroblastoma cells infected with HSV-1(F) or the R3616 mutant.

Figure 1B:
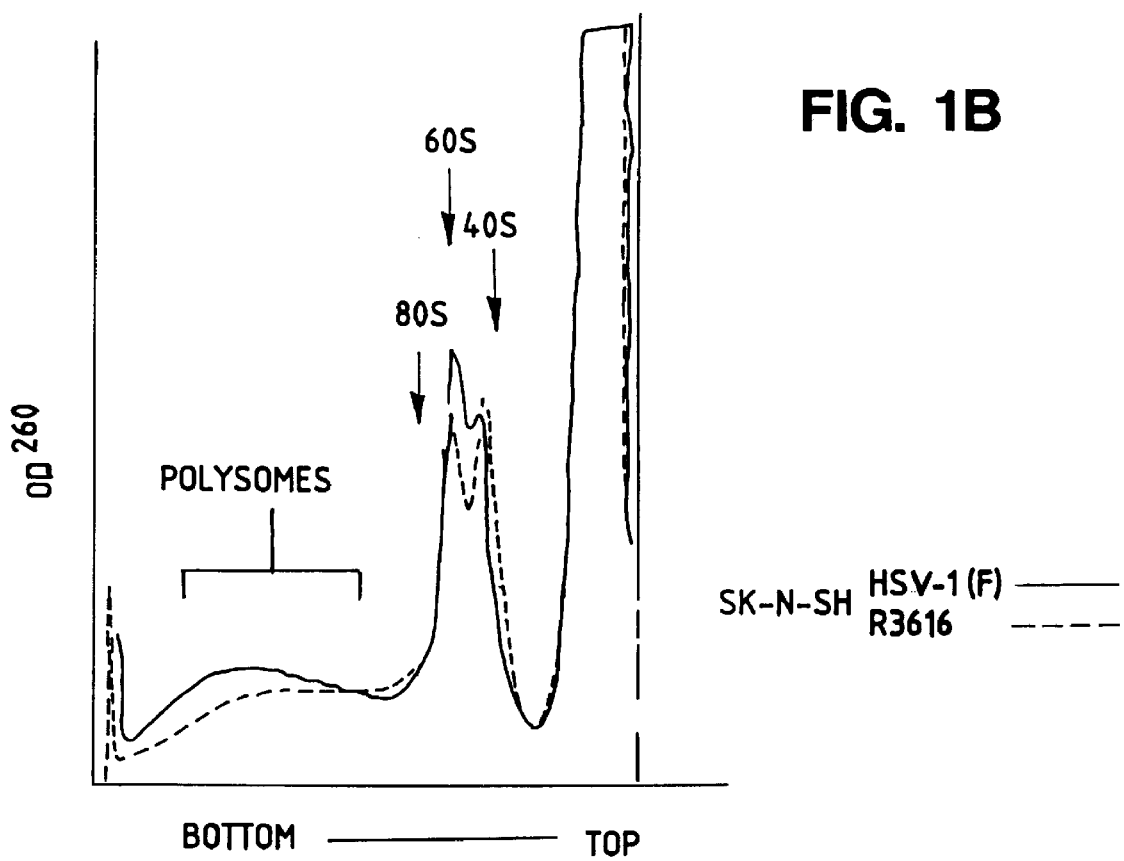

Replicate Vero cells or human SK-N-SH neuroblastoma cell cultures were infected with 5 PFU of wild type HSV-1(F) or R3616 ($\gamma_1 34.5^-$) virus described above. At 13 hrs after infection the cells were then harvested, rinsed with phosphate buffered saline and lysed with 0.5% of Triton X-100® surfactant. After brief centrifugation to remove the nuclei, the cytoplasm was loaded unto a 15%–50% w/w sucrose gradient and subjected to centrifugation at 40,000 rpm for 90 minutes at 4° C. in a Beckman ultracentrifuge in a SW41 rotor. After centrifugation, fractions were collected in a flow-through spectrophotometer and $OD_{260}$ was measured and recorded. FIGS. 1A & 1B show the spectrophotometric tracings of the separated ribosomal subunits and polyribosomes from infected cells. As shown in FIG. 1A, the sedimentation profiles of polyribosomes extracted from Vero cells infected with HSV-1(F) and R3616 were similar which is consistent with the observation that in Vero cells wild type and mutant viruses cannot be differentiated with respect to levels of intracellular protein synthesis. In contrast, the profile of polyribosomes from SK-N-H neuroblastoma cells infected with R3616 consists largely of 80S monosomes, 40S, and 60S ribosomal subunits, while the sedimentation profile of the cytoplasm of cells infected with wild type virus exhibited polyribosomes and substantially fewer monosomes and ribosomal subunits.

The sedimentation profiles of polyribosomes from SK-N-SH cells infected with R3616 are consistent with a gross decrease in the number of ribosomes engaged in translation of proteins late in infection. The most likely explanations for the observed phenomenon are: (a) a decrease in competent mRNA available for translation; or (b) a decrease in the rate of initiation of protein synthesis.

EXAMPLE 3

VIRAL MESSAGES ARE NOT DEGRADED IN HUMAN SK-N-SH NEUROBLASTOMA CELLS INFECTED WITH $\gamma_1 34.5^-$ VIRUS One hypothesis to explain the shutoff of protein synthesis in neuroblastoma cells infected with $\gamma_1 34.5^-$ virus is that viral mRNA is degraded in the absence of the $\gamma_1 34.5^-$ protein. To test this hypothesis, RNA transcripts, (either total RNA or purified poly $A^+$ mRNA) were obtained from SK-N-SH human neuroblastoma cells as follows. Replicate cultures were infected with HSV-1(F) or with R3616 viruses. At 13 hrs after infection the cells were harvested and the RNA was prepared from these cells using RNA STAT-60 kit from Tel-Test B, Inc. (Friendswood, Tex.) according to procedures specified by the manufacturer. Poly $A^+$ RNAs were then selected from total RNA with PolyA Tract mRNA Isolation Systems kit from Promega (Madison, Wis.). 5 µg of the total RNA and poly $A^+$ selected RNAs were then translated in vitro using a rabbit reticulocyte lysate system (Promega, Madison, Wis.) in the presence of $^{35}$S-methionine and an RNase inhibitor. The translated products were then solubilized, electrophoretically separated on a denaturing 10% polyacrylamide gel crosslinked with N'N'-diallyltartardiamide, transferred electrically unto a nitrocellulose membrane and subjected to autoradiography.

Figure 2:
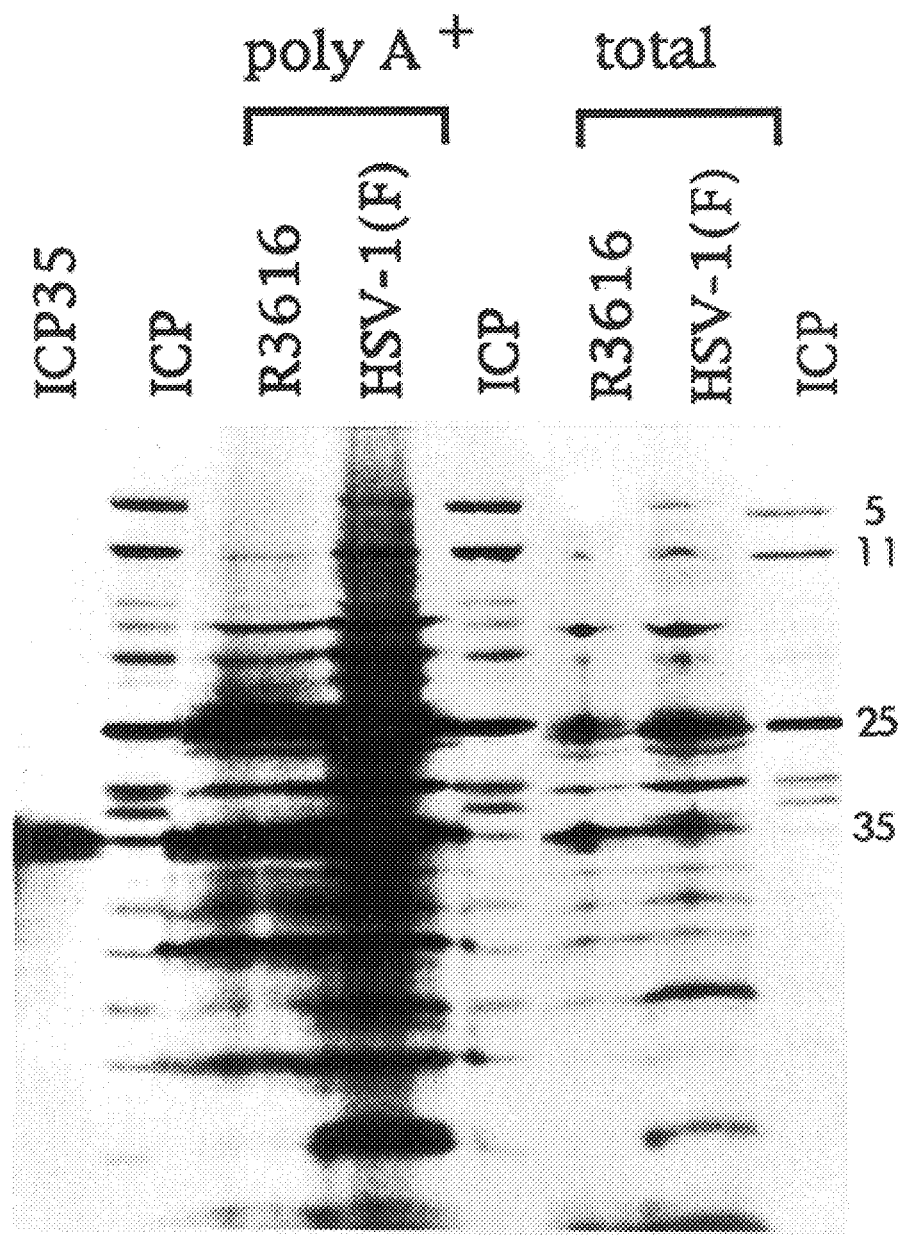
FIG. 2 depicts autoradiographic images of proteins translated in vitro from mRNA extracted from SK-N-SH cells infected with wild type and $\gamma_1 34.5^-$ viruses.

FIG. 2 shows the results of the analysis. The lanes marked ICP represent viral proteins specified by the wild type virus HSV-1(F) in infected Vero cells. The lane marked ICP35 contained the product of transcription and translation of the HSV-1 protease substrate encoded by the plasmid pRB4103 (Liu et al., *J. Virol.* 65:5149–5156 (1991)) by the SP6 transcription and translation kit provided by Promega. Both total and poly $A^+$ RNAs from cells infected with R3616 ($\gamma_1 34.5^-$) virus yielded all major viral proteins in a fashion similar to those expressed by RNA extracted from wild type infected cells. These results suggest that mRNA is not selectively degraded in $\gamma_1 34.5^-$ infected cells, but rather, that the transcripts present in $\gamma_1 34.5^-$ infected cells serve as functional templates for protein synthesis.

It is noteworthy that some proteins (e.g. ICP25 encoding the α trans-inducing factor or VP16 and members of the ICP35 family of proteins) were translated in vitro more efficiently than others (e.g. ICP5 and ICP11). On possible explanation for this phenomenon is that larger polypeptides tend to be prematurely terminated in in vitro systems.

EXAMPLE 4

AN EIF-2A KINASE ACTIVITY IS ASSOCIATED WITH THE RIBOSOMAL FRACTION IN CELLS INFECTED WITH $\gamma_1 34.5^-$ VIRUS In view of the results described in Example 3, another series of studies was conducted to determine whether the premature shutoff of protein synthesis in human neuroblastoma cells infected with R3616 is due to modification (phosphorylation) of α subunit of the translation initiation factor eIF-2 via eIF-2α kinase activity. The experiments utilized HeLa cells inasmuch as eIF-2 appears to be more stable in lysates of this cell line. HeLa cells, like most human cell lines studied to date, are also affected by premature shutoff of protein synthesis in cells infected with $\gamma_1 34.5^-$ viruses.

Figure 3A:
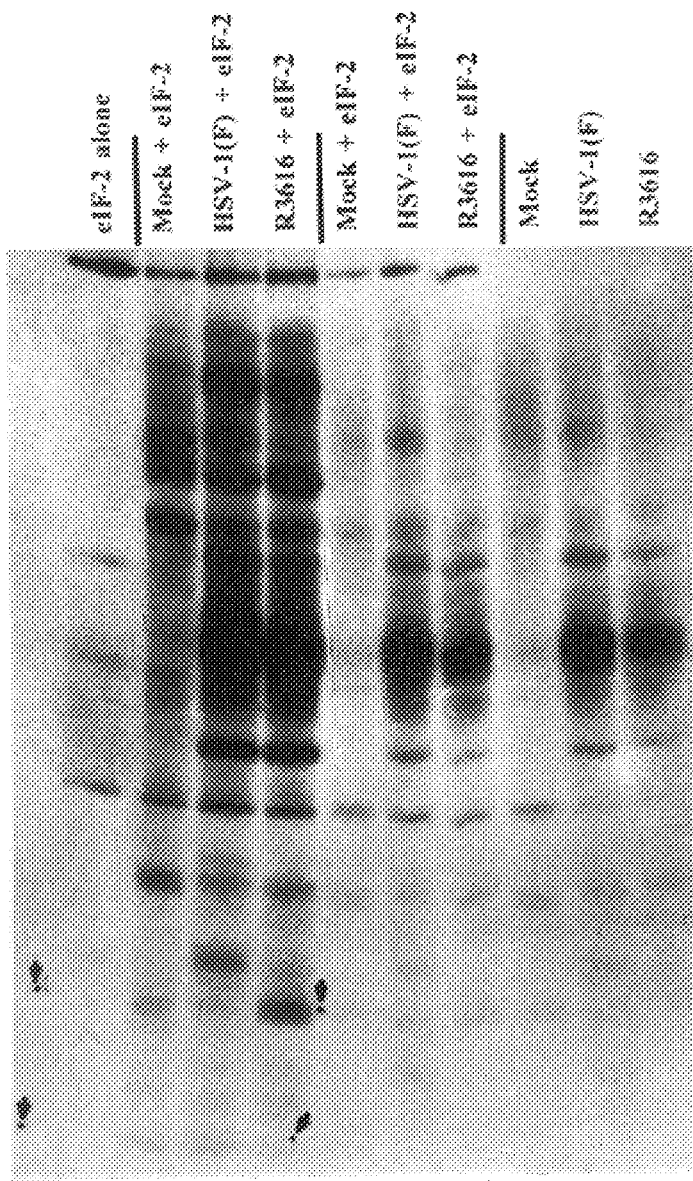
FIGS. 3A–3B illustrate eIF-2α kinase activity in infected cells and mock infected cell extracts.
Figure 3B:
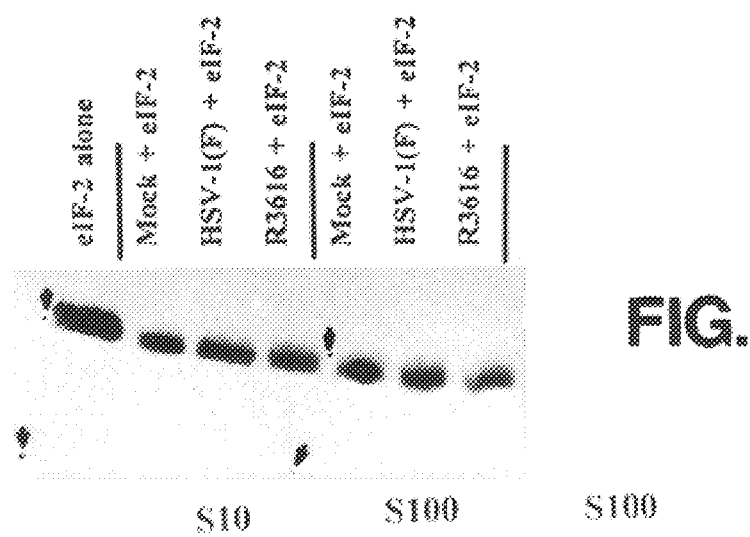

Replicate cultures of HeLa cells were either mock infected or infected with HSV-1(F) or R3616 viruses as described above. At 7 hrs after infection the cells were harvested and S10 fractions which includes all cytoplasmic materials (excluding mitochondria) were prepared according to procedures described by Pollard and Clemens (Pollard et al., *In Methods in Molecular Biology: New Nucleic Acid Techniques* (Walker, J. M., ed.), Chapter 5, pp.47–60, Humana Press, Clifton, N.J. (1988)). S100 fractions (post ribosomal) were supernatant fluids prepared from S10 fractions after centrifugation at 29,000 rpm for 3 hrs at 4° C. in a Beckman SW41 rotor. This fraction contained most of the soluble proteins but was free of ribosomes. Rabbit eIF-2 was purified from rabbit reticulocyte lysate according to the method describe by Grass et al., *J. Biol. Chem* ., 255:6270–6275 (1980) was used to detect the eIF-2α kinase activity present in those extracts. 0.2 µg of eIF-2 was reacted with the S10 or S100 fractions in the presence of [$\gamma^{32}$ P]-ATP (100 µCi per sample, Sp. act. 6000 Ci/mmol., NEN, Boston, Mass.) at 30° C. for 20 minutes. The reaction mixtures were then solubilized, electrophoretically separated on a denaturing 12% polyacrylamide gel crosslinked with N'N'-diallyltartardiamide, transferred unto nitrocellulose sheets and set for autoradiography as previously described (Chou et al., *Proc. Natl. Acad. Sci. USA* 89:3266–3270 (1992)). FIGS. 3A and 3B show the results of the analysis. Lanes with exogenous eIF-2 added were indicated on top. The position of eIF-2α is shown on the right.

As shown in FIG. 3A, eIF-2α subunit was extensively phosphorylated in the S10 extracts of R3616 infected cells, minimally phosphorylated in wild type- or mock-infected cells, and not phosphorylated at all in the absence of cell extracts. These results indicate that the S10 fraction of the γ₁34.5⁻ virus-infected cells contained an eIF-2α kinase activity that was much reduced or absent in similar extracts of mock-infected or wild type-infected cells. This activity was absent from all S100 fractions tested suggesting that the kinase activity is associated with ribosomes. In the absence of exogenous eIF-2, minimal phosphorylation of endogenous eIF-2 was observed in all extracts due to steady state phosphorylation and dephosphorylation processes in the cell.

FIG. 3B shows a photograph of nitrocellulose sheet containing separated proteins stained with monoclonal antibody specific to eIF-2α (Scorsone et al., *J. Biol. Chem.* 262:14538–14543 (1987)). After reacting with appropriate secondary antibody, the blot was developed with color reagents provided by Promega to identify the eIF-2α polypeptide. Arrows indicate the dots used to orient and align the phosphorylated eIF-2α polypeptide in FIG. 3A with the antibody stained eIF-2α polypeptide in FIG. 3B. The data in FIG. 3B shows that the level of eIF-2α was similar in all samples to which it had been added.

This activity was not present in mock-infected or wild type-infected cells. eIF-2 binds Met-tRNA$^f$ and GTP in a ternary complex which then associates with ribosomal subunits in a pre-initiation complex (Merrick, W. C., *Microbiological Reviews* 56:291–315 (1992); Hershey, J. W. B., *Annu. Rev. Biochem.* 60:717–755 (1991)). After initiation, eIF-2 is recycled off the 80S complex with the help of eIF-2B, another translational factor. One of the events which regulates translation is the phosphorylation of the α subunit of the eIF-2 complex. Phosphorylation of eIF-2α correlates with shut off of protein synthesis in heme-regulated hemopoietic cells, in response to growth inhibition, cellular stresses caused by virus infections, heat shock, heavy metals, deprivation of serum, amino acids, or glucose (Hershey, J. W. B., *Annu. Rev. Biochem.* 60:717–755 (1991); Sarre, T., *BioSystems* 22:311–325 (1989)). These effects have been linked to the phosphorylation of the ser$_{51}$ of eIF-2α either by PKR, a M$_r$ 68,000 a kinase also know as dsI, a double stranded RNA activated eIF-²α kinase which autophosphorylates itself, or by HRI, a heme regulated eIF-2α kinase (Merrick, W. C., *Microbiological Reviews* 56:291–315 (1992); Hershey, J. W. B., *Annu. Rev. Biochem.* 60:717–755 (1991)). A primary role of the phosphorylation of ser$_{51}$ in the regulation of protein synthesis is supported by the observation that substitution of the ser$_{51}$ with Ala precludes phosphorylation and maintains protein synthesis (Pathak et al., *Mol Cell Biol.* 8:993–995 (1988)).

EXAMPLE 5

PHOSPHORYLATION OF EIF-2A AND OF A M$_R$ 90,000 PROTEIN IN CELLS INFECTED WITH MUTANTS LACKING THE γ₁34.5 GENE OR CONTAINING A 3' TRUNCATION OF THE γ₁34.5 CODING SEQUENCE

Earlier studies have shown that the carboxyl terminal domain of γ₁34.5 is necessary to preclude the premature shutoff of protein synthesis in human neuroblastoma cell line whereas amino terminal domains of the protein were dispensable (Chou et al., *Proc. Natl. Acad. Sci. USA* 91:5247–5251 (1994)). To test the hypothesis that the PKR is the eIF-2α kinase activity described above and that this activity is elevated in cells infected with viruses containing truncations of carboxyl terminus of γ₁34.5 protein but not those carrying amino-terminal truncations of the protein, two series of experiments were done.

Figure 4A:
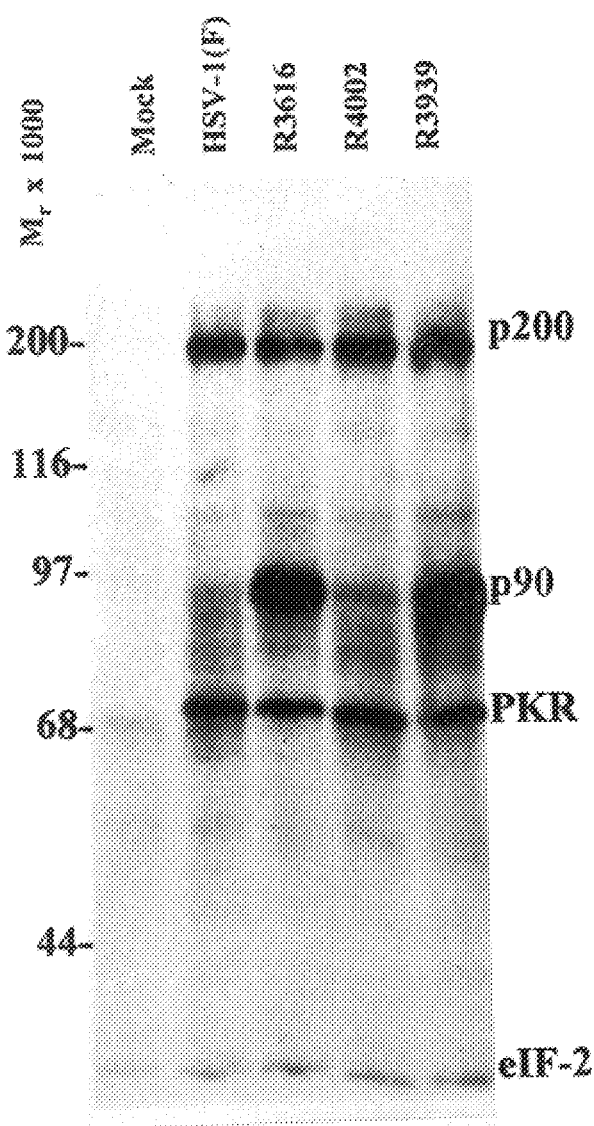
FIG. 4A depicts autoradiographic images of electrophoretically separated immunoprecipitates of PKR kinase.
Figure 4B:
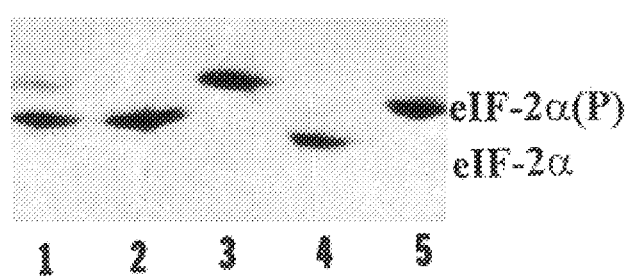
FIG. 4B depicts an immunoblot of eIF-2α separated by slab gel isoelectric focusing.
Figure 4C:
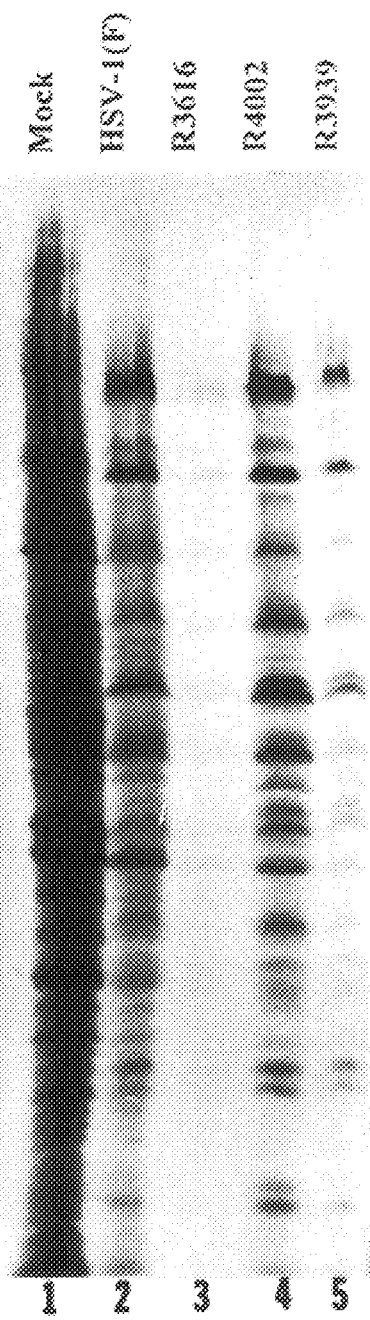
FIG. 4C depicts an autoradiographic image of electrophoretically separated proteins from lysates of HeLa cells infected with HSV-1(F), R3616, R4002, and R3936.

In one series of experiments, extracts containing endogenous eIF-2 from mock infected or infected HeLa cells were prepared in the presence of NaF to inhibit phosphatase activity and analyzed on slab isoelectric focusing gels to determine the extent of phosphorylation of eIF-2α. Sample preparation and all reagents used in this procedures are described in Maurides et al., *Anal. Biochem.* 183:144–151 (1989). HeLa cells grown in 6-well Costar dishes were mock infected or infected with the same viruses as described for 7 hours and the lysates were prepared in the presence of NaF to inhibit endogenous phosphatase activity. The lysate of approximately 2.5×10⁵ cells were loaded per lane and the gel were run overnight at room temperature in the pH gradient of 4.5 to 6.5, then electrically transferred to an Immobilon-P nylon membrane. eIF-2α was visualized by probing the membrane with monoclonal antibody specific for eIF-2α and developed with chemiluminescence reagents as specified by manufacturer (ECL, Amersham, Arlington Heights, Ill.). The eIF-2α(P) and eIF-2α, representing the phosphorylated and unphosphorylated species of eIF-2α respectively are identified to the right. Results are shown in FIG. 4B. Lanes 1–5 represent infection with the same viruses as shown in FIG. 4A. FIG. 4C Autoradiographic image of electrophoretically separated proteins from lysates of HeLa cells infected with the viruses described in FIG. 4A and identified at the top of each lane. The cells were mock infected or infected with 5 to 10 PFU/cell. At 12 hrs after infection the cells were labeled with [³⁵S]-methionine (20 μCi/sample, Sp. act. >1000 Ci/mmol. Amersham, Arlington Heights, Ill.) for 1 hr. The cells were then harvested, electrophoretically separated in denaturing gels as described in Panel A, transferred onto a nitrocellulose sheet and subjected to autoradiography. As shown in FIG. 4B, eIF-2α remained largely unphosphorylated or totally unphosphorylated in extracts of mock-infected cells (FIG. 4B, lane 1) or extracts of cells infected with wild type or mutant R4002 from which the first 28 codons of both copies of γ₁34.5 gene had been deleted (FIG. 4B, lane 2 and 4). As expected from earlier studies, these extracts were derived from cells fully competent to carry out protein synthesis as evident from [³⁵S]-methionine incorporation patterns shown in lanes 1, 2 and 4 of FIG. 4C. In contrast, eIF-2α was fully phosphorylated in extracts of HeLa cells infected with mutant R3616 carrying a 1000 bp deletion in γ₁34.5 gene or with mutant R3939 lacking the carboxyl terminus of γ₁34.5 (FIG. 4B, lane 3 and 5). The concordant finding was that protein synthesis reflected by incorporation of [³⁵]S methionine was largely shutoff in these cells (FIG. 4C lanes 3 and 5).

Experiments were performed to determine whether the phosphorylation of eIF-2α correlates with activation of PKR. S10 fractions were prepared as described in the legend to FIG. 2 form replicate cultures of HeLa cells that were either mock infected, or infected for 7 hours with wild type HSV-1(F) virus, R3616 carrying a 1000 bp deletion in the γ₁34.5 genes, R4002 carrying a deletion in the first 28 codons of the coding sequence of the γ₁34.5 genes, or R3936 carrying a deletion in the 3' domain of the γ₁34.5 gene were allowed to react with [γ³²]P-ATP (100 μCi per sample) for 20 minutes at 30° C. The fractions were then mixed with a rabbit polyclonal antibody specific for antibody to PKR purchased from Santa Cruz Biotechnology, Inc. Calif. The precipitated proteins were then collected, washed, solubilized, electrophoretically separated in a denaturing gel as described above, transferred unto nitrocellulose sheet and exposed to X-ray autoradiography. The positions of molecular weight standards (New England Biolabs, MA) are shown on the left.

As shown in FIG. 4A, lane 1, protein complexes precipitated by the PKR antibody from the mock cell extract were mostly unlabeled, whereas 3 or 4 phosphorylated polypeptides were precipitated from extracts of infected cells. These included PKR, a protein with an apparent $M_r$ of 200,000 (p200), and the α subunit of eIF-2 (FIG. 4A, lanes 2–5) suggesting PKR was activated in cells infected with all viruses, both mutant and wild type whereas eIF-2α was extensively phosphorylated only in cells infected with R3616 or R3939. However, in addition to these phosphoproteins, cells infected with R3616 or R3939 (FIG. 4A, lanes 3 and 5) contained an additional phosphorylated protein with an apparent $M_r$ of 90,000 (p90). This protein was not phosphorylated in cells infected with the wild type mutant or the mutant lacking the amino terminal 28 codons of the $\gamma_1$34.5 gene.

In summary, the immunoprecipitates of all infected cells contained PKR and a $M_r$200,000 (p200) protein. The immunoprecipitates of cells infected with total or carboxyl terminus deletion mutants of the $\gamma_1$34.5 gene contained in addition a heavily labeled $M_r$90,000 (p90) protein. Significantly more of the PKR enzyme was phosphorylated in cells infected with either wild type or $\gamma_1$34.5 mutants than in mock infected cells. These results indicate that elevation of PKR kinase activity may be a general characteristic of HSV-infected cells, a function induced by some unknown process occurring during infection.

Second, complete phosphorylation of the eIF-2α in lysates of cell infected with mutants lacking the sequences capable of encoding all or the carboxyl terminus of $\gamma_1$34.5 protein was particularly striking and does not appear to correlate with the levels of activated PKR. Numerous reports in the literature have shown that phosphorylation of as much as 30–60% of total cellular eIF-2α could account for the shutoff of 90–95% of total protein synthesis (Sarre, T., *BioSystems* 22:311–325 (1989)). Complete phosphorylation of the eIF-2α suggests that the mechanism for phosphorylation of eIF-2α is different from those described so far.

Lastly, the native function of p90 protein is not known, but the perfect correlation between the phosphorylation of p90 and the premature shutoff of protein synthesis exclusively in cells lacking either the entire $\gamma_1$34.5 gene or the domain coding the carboxyl terminus of the protein is particularly striking. The presence of phosphorylated p90 also correlates with the presence of excess activity capable of phosphorylating eIF-2α in exogenously added eIF-2. It would appear that in cells lacking a functional $\gamma_1$34.5 protein the p90 is a component of a complex containing PKR. It is possible that p90 regulates PKR activity in the phosphorylation of eIF-2α and that $\gamma_1$34.5 protein blocks this interaction. Further experiments to investigate the nature of p90 and its interaction with other proteins will shed light on the mechanism by which $\gamma_1$34.5 enables protein synthesis during HSV infection. This perfect correlation between the premature shutoff of protein synthesis and phosphorylation of p90 can exploit methods for screening candidate inducers or inhibitors of apoptosis.

EXAMPLE 6

METHODS FOR SCREENING CANDIDATE SUBSTANCES FOR INHIBITION OR INDUCTION OF APOPTOSIS

Both inducers and inhibitors of apoptosis have potential therapeutic value for a variety of diseases. For example, inducers of apoptosis may be used to kill tumor cells. In fact, as described above, one of the mechanisms by which chemotherapeutic agents can kill tumor cells is by inducing apoptosis. Inhibitors of apoptosis may be used to prevent cell death for example in neurodegenerative diseases such a Alzheimer's disease, Parkinson's disease, amyotrophic lateral sclerosis (Lou Gehrig's disease), and other neurodegenerative diseases.

The findings reported above that show that the shut down of cellular protein synthesis in response to apoptotic stress (for example infection with a $\gamma_1$, 34.5⁻ virus) is accompanied by an increase in the activity of PKR and the phosphorylation of eIF-2α and p90 can be exploited in methods for screening for inducers or inhibitors of apoptosis.

By way of example, candidate inducers of apoptosis may be screened by methods that utilize the procedures set out in Example 5 above in which it was demonstrated that infection of cells with $\gamma_1$ 34.5⁻ viruses resulted in shut down of cellular protein synthesis, increase in the activity of PKR, and phosphorylation of eIF-2α and p90. For the purposes of the screening method, instead of exposing the cells to the apoptotic stress using $\gamma_1$ 34.5⁻ virus, the cells may be exposed to other candidate inducers of apoptosis such as small molecules including but not limited to small peptides and other molecules. At a time or at a series of time points after exposure to the candidate inducer, cell lysates are analyzed as described in Example 5 above for the presence of phosphorylated eIF-2α and/or p90. Successful candidate inducers will be those substances which result in the phosphorylation of eIF-2α and/or p90. It should be noted that the appropriate dosage levels of the candidate inducer will vary as will the time of exposure to the candidate inducer. Dosages and exposure time levels may be readily determined by one or ordinary skill in the art as well as the particular timing between exposure of the cells to the inducer and the analysis of eIF-2α and p90.

It should also be noted that candidate inducers of apoptosis need not be limited to chemical substances but may also include perturbations of the environmental conditions to which the cells are exposed, exposure to electromagnetic radiation, depletion of growth factors, or physical manipulations and other perturbations.

Similar procedures may be used in a method of screening for inhibitors of apoptosis. In such a method, duplicate cultures of HeLa cells or other cells as described above are set up to serve as test cells and control cells. The test cells are then exposed to a candidate apoptosis inhibitor. Both the test cells and the control cells are then exposed to an apoptotic stress (for example infection with an $\gamma_1$ 34.5⁻ virus as described above or other known apoptotic stresses). After a period of time, both the test cells and control cells are analyzed for the levels of phosphorylation of eIF-2α and/or p90 using methods described above.

Inhibitors of apoptosis are identified by a decrease in the ability of cells exposed to the inhibitor to phosphorylate eIF-2α and/or p90 when compared to control cells.

EXAMPLE 7

CLONING OF DNA ENCODING p90

As described above, p90 is a novel protein whose phosphorylation correlates with the shut down of protein synthesis associated with apoptotic stress. Cloning of DNA encoding p90 will permit the increased production of the protein over the endogenous levels found in eucaryotic cells. The availability of increased quantities of p90 will permit a more detailed study of its role in the shut down of protein synthesis and will permit the development of new more sensitive assays for the screening of candidate inhibitors and inducers of apoptosis. The p90 protein itself may be useful as an inducer of apoptosis when administered to cells such as tumor cells which may have lost their ability to produce an active p90.

Vectors e.g. viruses, plasmids, cosmids are and other vectors comprising the DNA encoding p90 may also be used to introduce p90 encoding DNA into cells for the purpose of inducing apoptosis into cells having a defective p90. The expressed p90 protein may exert its activity after phosphorylation by endogenous kinases such as PKR or may be co-transferred with vectors comprising DNA encoding the appropriate kinases.

Cloning of the DNA encoding p90 may be accomplished using any of a variety of well known techniques. Such cloning techniques are set out in standard references such as Sambrook et al., *Molecular Cloning, A Laboratory Manual*, Second Edition, Cold Spring Harbor Laboratories, Cold Spring Harbor, N.Y., 1989, and *Current Protocols in Molecular Biology*, Ausubel et al. Eds. John Wiley and Sons, Inc. 1994.

Of particular applicability of cloning of the DNA encoding p90 is the two-hybrid system of cloning describe in Fields et al., *Nature*, 340:245–246 (1989) and Chien et al., *Proc. Nat'l. Acad. Sci. (USA)*, 88:9578–9582 (1991). The two-hybrid system is particularly useful for cloning genes encoding protein that interact with a protein of interest.

We claim:

1. A method of screening candidate inhibitors of programmed cell death, the method comprising the steps of:
   (a) preparing duplicate cell cultures;
   (b) exposing one of the duplicate cell cultures to a candidate inhibitor;
   (c) exposing the duplicate cell cultures to an inducer of programmed cell death;
   (d) preparing respective cell lysates from the duplicate cell cultures of step (c);
   (e) contacting the lysates of step (d) with ATP wherein the γ phosphate of the ATP has a detectable label; and
   (f) measuring the levels of phosphorylated p90 and/or eIF-2α produced by the lysates;
   whereby inhibitors of programmed cell death are identified by their ability to prevent or decrease phosphorylation of eIF-2α and/or p90 when compared to the level of phosphorylation of eIF-2α and/or p90 in cells not exposed to the candidate substance.

2. The method of claim 1 wherein the cells are human cells.

3. The method of claim 2 wherein the human cells are selected from the group consisting of HeLa cells, SK-N-SH neuroblastoma cells, and human foreskin fibroblasts.

4. The method of claim 1 wherein the programmed cell death is induced by infection with a herpes simplex virus lacking $\gamma_1 34.5$ genes capable of expressing an active gene product.

5. The method of claim 1 wherein the ATP is $\gamma^{32}$P-ATP.

6. The method of claim 1 wherein the levels of phosphorylated eIF-2α and/or p90 are measured by the steps of:
   precipitating eIF-2α and/or p90 from the cell lysates using an antibody directed to PKR;
   separating precipitated eIF-2α and/or p90 by electrophoresis on denaturing gels;
   transferring the separated eIF-2α and/or p90 onto an immobilizing membrane;
   exposing the membrane to X-ray film;
   developing the X-ray; and
   measuring the intensities of the eIF-2α specific signal and the p90 specific signal generated from the duplicate cell cultures.

7. A method for screening candidate inducers of programmed cell death the method comprising the steps of:
   (a) preparing duplicate cell cultures;
   (b) exposing one of the duplicate cell cultures to a candidate inducer of programmed cell death;
   (c) preparing respective cell lysates from the cell culture exposed to the candidate inducer and from the unexposed cell culture;
   (d) contacting the lysates with ATP wherein the γ phosphate of the ATP has a detectable label; and
   (e) measuring the levels of phosphorylated p90 and/or eIF-2α produced in the lysates;
   whereby inducers of programmed cell death are identified by their ability to increase phosphorylation of eIF-2α and/or p90 in the lysates of exposed cells when compared to lysates from unexposed cells.

8. The method of claim 7 wherein the cells are human cells.

9. The method of claim 8 wherein the cells are selected from the group consisting of HeLa cells, SK-N-SH neuroblastoma cells, and foreskin fibroblasts.

10. The method of claim 7 wherein the ATP is $\gamma^{32}$P-ATP.

11. The method of claim 7 wherein the levels of phosphorylated eIF-2α and/or p90 are measured by the steps of:
    precitipating eIF-2α and/or p90 from the cell lysates using an antibody directed to PKR;
    separating precipitated PKR-kinase, eIF-2α and/or p90 by electrophoresis on denaturing gels;
    transferring the separated PKR-kinase, eIF-2α and/or p90 onto an immobilizing membrane;
    exposing membrane to X-ray film:
    developing the X-ray film; and
    measuring the intensities of the PKR-kinase, eIF-2α specific signal and/or p90 specific signal generated in the duplicate cell cultures.

12. A method of screening candidate inhibitors of programmed cell death, the method comprising the steps of:
    (a) preparing duplicate cell cultures;
    (b) exposing one of the duplicate cell cultures to a candidate inhibitor;
    (c) exposing the duplicate cultures to an inducer of programmed cell death; and,
    (d) measuring the levels of phosphorylated p90 and/or eIF-2α in each of the duplicate cell cultures;
    whereby inhibitors of programmed cell death are identified by their ability to prevent or decrease the level of phosphorylation of eIF-2α and/or p90 when compared to the level of phosphorylation of eIF-2α and/or p90 in cells not exposed to the candidate inhibitor.

13. The method of claim 12 further comprising the steps of:
    (e) exposing duplicate cell cultures of step (c) to [$^{35}$S]-methionine;
    (f) preparing a lysate of the duplicate cell cultures of step (e);
    (g) separating the phosphorylated and unphoshorylated eIF-2α and/or p90 contained in the lysate from other constituents of the lysate; and (h) measuring the level of $^{35}$S-labelled phosphorylated and unphosphorylated eIF-2α and/or p90;

whereby an inhibitor of programmed cell death is identified by its ability to decrease or inhibit the phosphorylation of eIF-2α and/or p90.

14. The method of claim 13 wherein said phosphorylated and unphosphorylated eIF-2α and/or p90 are separated from other constituents of the lysate by polyacrylamide gel electrophoresis.

15. A method for screening candidate inducers of programmed cell death, the method comprising the steps of:

(a) preparing duplicate cell cultures;

(b) exposing one of the duplicate cultures to a candidate inducer of programmed cell death; and (c) measuring the levels of phosphorylated eIF-2α and/or p90 in each of the duplicate cultures;

wherein an inducer of programmed cell death is identified by its ability to increase the level of phosphorylation of eIF-2α and/or p90.

16. The method of claim 15 further comprising the steps of:

(d) exposing said duplicate cultures of steps (a) and (b) to [$^{35}$S]-methionine;

(e) preparing a lysate of each of the duplicate cell cultures of step (d);

(f) separating the phosphorylated and unphoshorylated eIF-2α and/or p90 contained in the lysates from other constituents of the lysates; and (g) measuring the relative $^{35}$S-labelled phosphorylated and unphosphorylated eIF-2α and/or p90;

whereby an inducer of programmed cell death is identified by its ability to increase the level of phosphorylation of eIF-2α and/or p90.

17. The method of claim 16 wherein said phosphorylated and unphosphorylated eIF-2α and/or p90 are separated from other constituents of the lysates by polyacrylamide gel electrophoresis.

* * * * *